United States Patent
Difiore

(10) Patent No.: US 9,993,633 B2
(45) Date of Patent: Jun. 12, 2018

(54) GRAFT-CATHETER VASCULAR ACCESS SYSTEM

(71) Applicant: C. R. Bard, Inc., Murray Hill, NJ (US)

(72) Inventor: Attilio E. Difiore, Taylorsville, UT (US)

(73) Assignee: C. R. Bard, Inc., Murray Hill, NJ (US)

( * ) Notice: Subject to any disclaimer, the term of this patent is extended or adjusted under 35 U.S.C. 154(b) by 849 days.

(21) Appl. No.: 13/715,952

(22) Filed: Dec. 14, 2012

(65) Prior Publication Data

US 2013/0102950 A1    Apr. 25, 2013

Related U.S. Application Data

(62) Division of application No. 09/333,637, filed on Jun. 15, 1999, now Pat. No. 9,814,869.

(51) Int. Cl.
| | |
|---|---|
| *A61M 39/10* | (2006.01) |
| *A61B 17/11* | (2006.01) |
| *A61L 31/04* | (2006.01) |
| *A61L 31/06* | (2006.01) |
| *A61L 31/10* | (2006.01) |

(Continued)

(52) U.S. Cl.
CPC ............. *A61M 39/10* (2013.01); *A61B 17/11* (2013.01); *A61L 31/048* (2013.01); *A61L 31/06* (2013.01); *A61L 31/10* (2013.01); *A61M 1/3655* (2013.01); *A61B 2017/1107* (2013.01); *A61B 2017/1135* (2013.01); *A61F 2/064* (2013.01)

(58) Field of Classification Search
USPC ............. 606/8, 151, 153, 155; 623/1.1, 903; 604/8
See application file for complete search history.

(56) References Cited

U.S. PATENT DOCUMENTS

| | | |
|---|---|---|
| 2,935,068 A | 5/1960 | Donaldson |
| 3,094,124 A | 6/1963 | Birtwell |

(Continued)

FOREIGN PATENT DOCUMENTS

| | | |
|---|---|---|
| CA | 2377483 A1 | 12/2000 |
| DE | 4418910 A1 | 12/1995 |

(Continued)

OTHER PUBLICATIONS

A.S. Coulson, M.D., Ph.D. et al, A Combination of the Elephant Trunk Anastomosis Technique and Vascular Clips for Dialysis Grafts, Surgical Rounds, pp. 596-608, Nov. 1999.

(Continued)

*Primary Examiner* — Brian Pellegrino
(74) *Attorney, Agent, or Firm* — Rutan & Tucker, LLP

(57) ABSTRACT

A vascular access device, for implantation at least partially below the skin of a patient to provide an arteriovenous fistula, includes a graft portion coupled to a catheter portion. The graft portion is sutured to an opening in an artery while the catheter portion is inserted into a vein so that its end lies within the vein downstream from the point of entry into the vein. The device may be comprised of ePTFE with an outer polyurethane coating or the graft portion may comprise ePTFE with an outer polyurethane coating and the catheter portion may comprise polyurethane. There may also be an inner polyurethane coating. Alternatively, the device may be comprised entirely of polyurethane.

2 Claims, 4 Drawing Sheets

(51) Int. Cl.
*A61M 1/36* (2006.01)
*A61F 2/06* (2013.01)

(56) References Cited

U.S. PATENT DOCUMENTS

| | | |
|---|---|---|
| 3,638,649 A | 2/1972 | Ersek |
| 3,683,926 A | 8/1972 | Suzuki |
| 3,713,441 A | 1/1973 | Thomas |
| 3,818,511 A | 6/1974 | Goldberg et al. |
| 3,826,257 A | 7/1974 | Buselmeier |
| 3,853,126 A | 12/1974 | Schulte |
| 3,882,862 A | 5/1975 | Berend |
| 4,076,023 A | 2/1978 | Martinez |
| 4,119,094 A | 10/1978 | Micklus et al. |
| 4,318,401 A | 3/1982 | Zimmerman |
| 4,447,237 A | 5/1984 | Frisch et al. |
| 4,496,349 A | 1/1985 | Cosentino |
| 4,632,668 A | 12/1986 | Wilson, Jr. et al. |
| 4,790,826 A | 12/1988 | Elftman |
| 4,822,341 A | 4/1989 | Colone |
| 4,898,591 A | 2/1990 | Jang et al. |
| 4,898,669 A | 2/1990 | Tesio |
| 4,929,236 A | 5/1990 | Sampson |
| 5,041,098 A | 8/1991 | Loiterman et al. |
| 5,090,954 A | 2/1992 | Geary |
| 5,152,782 A | 10/1992 | Kowligi et al. |
| 5,165,952 A | 11/1992 | Solomon et al. |
| 5,188,593 A * | 2/1993 | Martin ........................... 604/43 |
| 5,192,310 A | 3/1993 | Herweck et al. |
| 5,298,276 A | 3/1994 | Jayaraman |
| 5,300,032 A | 4/1994 | Hibbs et al. |
| 5,330,528 A | 7/1994 | Lazim |
| 5,399,168 A | 3/1995 | Wadsworth, Jr. et al. |
| 5,399,352 A | 3/1995 | Hanson |
| 5,454,373 A | 10/1995 | Koger et al. |
| 5,456,714 A | 10/1995 | Owen |
| 5,476,451 A | 12/1995 | Ensminger et al. |
| 5,558,641 A | 9/1996 | Glantz et al. |
| 5,562,618 A | 10/1996 | Cai et al. |
| 5,571,167 A | 11/1996 | Maginot |
| 5,591,226 A | 1/1997 | Trerotola et al. |
| 5,637,088 A | 6/1997 | Wenner et al. |
| 5,637,102 A | 6/1997 | Tolkoff et al. |
| 5,651,767 A | 7/1997 | Schulman et al. |
| 5,676,346 A | 10/1997 | Leinsing |
| 5,676,670 A | 10/1997 | Kim |
| 5,687,718 A | 11/1997 | Fischer et al. |
| 5,743,894 A | 4/1998 | Swisher |
| 5,755,775 A | 5/1998 | Trerotola et al. |
| 5,782,811 A | 7/1998 | Samson et al. |
| 5,792,104 A | 8/1998 | Speckman et al. |
| 5,797,879 A | 8/1998 | DeCampli |
| 5,797,920 A | 8/1998 | Kim |
| 5,800,514 A | 9/1998 | Nunez et al. |
| 5,800,522 A | 9/1998 | Campbell et al. |
| 5,830,222 A | 11/1998 | Makower |
| 5,830,224 A | 11/1998 | Cohn et al. |
| 5,849,036 A | 12/1998 | Zarate |
| 5,861,026 A | 1/1999 | Harris et al. |
| 5,879,320 A | 3/1999 | Cazenave |
| 6,017,577 A | 1/2000 | Hostettler et al. |
| 6,019,786 A | 2/2000 | Thompson |
| 6,019,788 A | 2/2000 | Butters et al. |
| 6,102,884 A | 8/2000 | Squitieri |
| 6,159,141 A | 12/2000 | Apple et al. |
| 6,261,255 B1 | 7/2001 | Mullis et al. |
| 6,261,257 B1 | 7/2001 | Uflacker et al. |
| 6,338,724 B1 | 1/2002 | Dossa |
| 6,436,135 B1 | 8/2002 | Goldfarb |
| 6,582,409 B1 | 6/2003 | Squitieri |
| 6,585,762 B1 | 7/2003 | Stanish |

FOREIGN PATENT DOCUMENTS

| | | |
|---|---|---|
| EP | 1185330 A1 | 3/2002 |
| JP | 55152728 A | 11/1980 |
| JP | 1071208 A | 3/1989 |
| JP | 02147065 A | 6/1990 |
| JP | 05176948 A | 7/1993 |
| JP | 10505266 T | 5/1998 |
| JP | 2003501223 A | 1/2003 |
| JP | 4975918 | 4/2012 |
| MX | PA01012954 A | 6/2003 |
| WO | 1997031590 A1 | 9/1997 |
| WO | 1997031591 A1 | 9/1997 |
| WO | 1998034676 A1 | 8/1998 |
| WO | 1998052495 A1 | 11/1998 |
| WO | 2000057814 A1 | 10/2000 |
| WO | 2000076577 A1 | 12/2000 |

OTHER PUBLICATIONS

Alan S. Coulson, M.D et al, Modification of Venous End of Dialysis Grafts: An Attempt to Reduce Neointimal Hyperplasia, Dialysis & Transplantation, vol. 29 No. 1, pp. 10-18, Jan. 2000.

Bonnaud, Philippe et al, Le Carboclip® un nouvel acces vasculaire atraumatique pour hemodialyse, Nephrologie vol. 15, 1994.

D. Vorwerk et al, Nathfreie vaskulare End-zu-Seit-Anastomose: In-vivo-Test eines perkutanen Konzeptes im Tier-modell, Fortschr, Rontgenstr., pp. 83-86, 1671, 1997.

E. Petrella et al, A New End-to-End Anastomosis Formed Sutures for Haemodialysis Arteriovenous Fistuals, Nephron, vol. 14 pp. 398-400, 1975.

JP 2001-502907 filed Jun. 15, 2000 Office Action dated Jan. 6, 2011.

JP 2001-502907 filed Jun. 15, 2000 Office Action dated Nov. 1, 2011.

K. Sumimoto et al, Non-suture end-to-end anastomoses between polytetrafluorethylene graft and vessels for blood access, Panminerva Medica, pp. 72-77, Mar. 1999.

Marc A. Borge, MD et al , Percutaneous Ablation of a Pancreatic Remnant with Intraductal Injection of Neoprene, Journal of Vascular and Interventional Radiology, pp. 762-764, Sep.-Oct. 1995.

PCT/US2000/016623 filed Jun. 15, 2000 International Preliminary Examination Report dated Sep. 9, 2001.

PCT/US2000/016623 filed Jun. 15, 2000 Search Report dated Oct. 6, 2000.

PCT/US2000/016623 filed Jun. 15, 2000 Written Opinion dated Oct. 6, 2000.

Philippe Bonnaud et al, Clinique Bizet, Paris, Departement de Nephrologie, INSERM U90, Hopital Necker, Paris.

The Consumer Committee of the Southeastern Kidney Council (ESRD Network 6), "Vascular Access for Hemodialysis", 16 pages, 1999.

U.S. Appl. No. 09/333,637, filed Jun. 15, 1999 Advisory Action dated Jul. 1, 2010.

U.S. Appl. No. 09/333,637, filed Jun. 15, 1999 Advisory Action dated Jun. 5, 2002.

U.S. Appl. No. 09/333,637, filed Jun. 15, 1999 Advisory Action dated Jun. 6, 2007.

U.S. Appl. No. 09/333,637, filed Jun. 15, 1999 Advisory Action dated Mar. 20, 2003.

U.S. Appl. No. 09/333,637, filed Jun. 15, 1999 Advisory Action dated Sep. 23, 2005.

U.S. Appl. No. 09/333,637, filed Jun. 15, 1999 Final Office Action dated Apr. 27, 2010.

U.S. Appl. No. 09/333,637, filed Jun. 15, 1999 Final Office Action dated Aug. 22, 2011.

U.S. Appl. No. 09/333,637, filed Jun. 15, 1999 Final Office Action dated Feb. 26, 2007.

U.S. Appl. No. 09/333,637, filed Jun. 15, 1999 Final Office Action dated Jan. 12, 2005.

U.S. Appl. No. 09/333,637, filed Jun. 15, 1999 Final Office Action dated Jan. 14, 2003.

U.S. Appl. No. 09/333,637, filed Jun. 15, 1999 Final Office Action dated Jun. 4, 2008.

U.S. Appl. No. 09/333,637, filed Jun. 15, 1999 Final Office Action dated Mar. 8, 2002.

U.S. Appl. No. 09/333,637, filed Jun. 15, 1999 Final Office Action dated Oct. 18, 2012.

(56) References Cited

OTHER PUBLICATIONS

U.S. Appl. No. 09/333,637, filed Jun. 15, 1999 Non-Final Office Action dated Aug. 23, 2002.
U.S. Appl. No. 09/333,637, filed Jun. 15, 1999 Non-Final Office Action dated Dec. 14, 2005.
U.S. Appl. No. 09/333,637, filed Jun. 15, 1999 Non-Final Office Action dated Jan. 21, 2011.
U.S. Appl. No. 09/333,637, filed Jun. 15, 1999 Non-Final Office Action dated Jul. 27, 2004.
U.S. Appl. No. 09/333,637, filed Jun. 15, 1999 Non-Final Office Action dated May 15, 2012.
U.S. Appl. No. 09/333,637, filed Jun. 15, 1999 Non-Final Office Action dated May 25, 2001.
U.S. Appl. No. 09/333,637, filed Jun. 15, 1999 Non-Final Office Action dated Nov. 2, 2007.
U.S. Appl. No. 09/333,637, filed Jun. 15, 1999 Non-Final Office Action dated Nov. 4, 2003.
U.S. Appl. No. 09/333,637, filed Jun. 15, 1999 Non-Final Office Action dated Sep. 29, 2009.
Yukio Kuniyoshi et al, A New Devised Skirted Elephant Trunk-Technique, Ann Thorac Cardiovasc Surg, vol. 5, No. 1 pp. 56-58, 1999.

* cited by examiner

GRAFT-CATHETER VASCULAR ACCESS SYSTEM

PRIORITY

This application is a division of U.S. patent application Ser. No. 09/333,637, filed Jun. 15, 1999, now U.S. Pat. No. 9,814,869, which is incorporated by reference in its entirety into this application.

BACKGROUND OF THE INVENTION

Field of the Invention

The present invention relates to medical devices, and more particularly, to a device that provides an improved method for vascular access.

Description of Related Art

Providing frequent, direct, vascular access has become a necessity for many medical procedures including hemodialysis, chemotherapy, various tests requiring frequent blood draws and treatments requiring frequent intravenous administration of drugs. Many vascular access devices have been developed to meet this need. Often the devices are permanently inserted into the patient, but such devices have experienced a variety of problems. For example, the arteriovenous shunt includes a length of silicone rubber tubing bearing catheter tips at each end that are respectively inserted into an artery and a vein below the skin while the remaining tubing extends beyond the skin surface. This design is plagued by infection and clotting problems at the sites where the tubing passes through the skin surface. External shunts further pose an inconvenience to the patient because of the extra care that is required to avoid snagging the exposed tubing which could result in injury to the skin and to dislodging the device.

Another method of vascular access utilizes a subcutaneous autologous arteriovenous fistula that is formed by suturing a native artery to a native vein to create a high volume of blood flow in the vein. Arterial pressure causes contiguous veins to dilate and provide sites for venipuncture. However, such a fistula may not be used for several weeks after formation because significant time is required for the walls of the dilated vein to thicken sufficiently. In addition, the required, repeated needle punctures eventually weaken and destroy the arterialized vein, which, to begin with, is subject to abnormal pressurization and is particularly susceptible to collapse.

As alternatives, expanded polytetrafluoroethylene (ePTFE) bridge grafts and dual lumen venous catheters have been developed. The ePTFE bridge graft creates a loop between an artery and a vein, by suturing one end of the graft to an artery and the other end to a vein, but this device is prone to complications such as thrombosis, infection, and infiltration of scar-forming cells. After insertion, the ePTFE graft must be allowed to mature or heal prior to needle puncture, because ePTFE grafts are highly porous. After sufficient healing, surrounding body tissues grow into the walls of the ePTFE graft to provide a limited ability to self-seal. This healing process takes approximately two weeks in most patients. Failure to allow the ePTFE graft to mature or heal often results in hematoma formation, false aneurysm, leaking of blood from the needle puncture site, and/or early fistula failure. Perhaps the most significant complication, though, is neointimal hyperplasia that often occurs near the venous anastomosis and eventually leads to thrombosis of the graft.

With the dual lumen venous catheter, the catheter is percutaneously inserted into a central vein. Numerous complications occur with this method due to the lack of a continuous blood flow such as with the ePTFE bridge graft. These complications may include poor flow rates due to kinking or recurrent thrombosis secondary to stasis of blood in the lumen and build up of fibrinous debris at the venous end. Also, as with the external shunt described above, infection at the entry site at the skin may occur and extra care is required to avoid injury or dislodging the tubing.

Shunt devices are also known that avoid percutaneous needle punctures by providing a skin level port with connections to an artery and a vein through ePTFE tubing. These devices, as above, present the risk of infection at the skin surface and require extra care. Also, discontinuities of the blood flow path often cause a buildup of clotted blood that may restrict or ultimately seal off the flow of blood therethrough, resulting in thrombosis.

Accordingly, it would be desirable to provide a vascular access device having superior patency rates along with minimal complications in its use. The device would avoid skin surface infections, provide continuous, strong, blood flow rates to prevent thrombosis, and minimize damage to the vascular system and associated problems such as hyperplasia. Furthermore, the device would provide immediate, easy, needle access for long-term vascular access, which is required for various medical procedures such as hemodialysis and frequent blood draws.

SUMMARY OF THE INVENTION

In accordance with the teachings of the present invention, a graft-catheter is provided. The graft-catheter provides an improved method of vascular access by eliminating many of the complications of prior art devices. The graft-catheter can be implanted subcutaneously thereby eliminating skin level infections. The device connects an artery to a vein providing continuous blood flow to help prevent thrombosis and avoiding venous anastomosis so as to prevent hyperplasia. The graft-catheter combines the beneficial qualities of both a graft and a catheter to achieve a superior vascular access device that allows immediate needle access for a variety of medical procedures.

The vascular access device, for implantation at least partially below the outer skin of a patient, comprises a graft portion and a catheter portion both having tubular walls. The graft portion has a first end that is to be coupled to a first blood vessel and a second end that couples with a first end of the catheter portion. The second end of the catheter portion is inserted into a second blood vessel. The graft portion may further comprise a tapered portion that narrows in diameter to transition from a diameter of the graft portion to a diameter of the catheter portion. The catheter portion may further comprise a plurality of transverse holes in the tubular wall adjacent to the second end, with the second end being beveled for ease of insertion into the second blood vessel. The graft portion may further comprise at least one needle receiving port and the catheter portion may further comprise a dual lumen configuration.

In a first embodiment of the present invention, the graft portion and the catheter portion are comprised of ePTFE and the catheter portion further comprises an outer coating of polyurethane. The graft portion may also comprise an outer polyurethane coating. The graft portion and the catheter portion may comprise a unitary construction of ePTFE and may further include an inner polyurethane coating.

In a second embodiment of the present invention, the graft portion is comprised of ePTFE and the catheter portion is comprised of polyurethane. The graft portion may further comprise an outer polyurethane coating. The coupling of the graft portion to the catheter portion may comprise at least one of an injection-molded process, a sutured seam, and an adhesive bond. The graft portion and catheter portion may further comprise an inner polyurethane coating.

In a third embodiment of the present invention, the graft portion and the catheter portion are comprised of polyurethane. The coupling of the graft portion and the catheter portion may comprise at least one of a molding process, an adhesive bond, and a sutured seam. Alternatively, the graft portion and the catheter portion may comprise a unitary construction of polyurethane.

For the various embodiments of the present invention, the polyurethane coating or polyurethane material may comprise at least one of a polyether, a polyester, and a polycarbonate, with a durometer value between 70 A and 65 D. The polyurethane coating or polyurethane material may also comprise at least one of a surface modifying end group, a surface modifying macromolecule, an anti-coagulant agent, an ion beam implantation, a gas plasma treatment, a depth marking, a radiopaque strip, a radiopaque additive, an echogenic coating, and a hydrogel such as a polyvinylpyrrolodon, a polyethyleneglycol, and/or a polyethyleneoxide.

A more complete understanding of the vascular access device will be afforded to those skilled in the art, as well as a realization of additional advantages and objects thereof, by a consideration of the following detailed description of the preferred embodiment. Reference will be made to the appended sheets of drawings that will first be described briefly.

DETAILED DESCRIPTION OF THE PREFERRED EMBODIMENT

Figure 1:
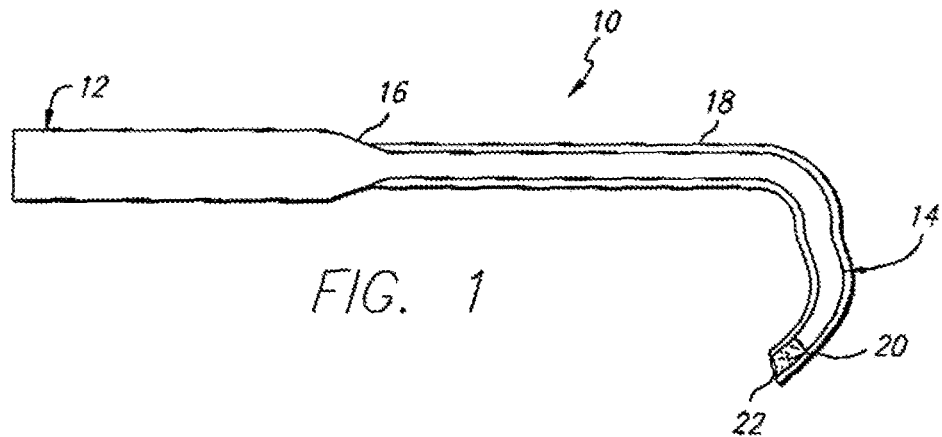
FIG. 1 is a side sectional view in accordance with a first embodiment of the present invention.

The present invention satisfies the need for a graft-catheter device that provides an improved method for vascular access. In the detailed description that follows, it should be appreciated that like reference numerals are used to identify like elements illustrated in one or more of the figures.

Referring first to FIG. 1, a side sectional view of a graft-catheter 10 in accordance with a first embodiment of the present invention is illustrated. The graft-catheter 10 has a graft section 12 and a catheter section 14 that is long and flexible. The graft section 12 transitions to the catheter section 14 at a tapered region 16. The diameter of the graft section 12 and the catheter section 14 will vary depending upon the size of the patient and the corresponding artery and vein selected. As an example, the diameter of the graft section 12 may be 5-8 millimeters (mm), the tapered region 16 will taper in diameter over a short segment of the graft-catheter 10, and the diameter of the catheter section 14 may be 2-5 mm. The catheter section 14 may have a plurality of transverse holes 20 for optimal blood dispersion and a beveled end 22 for ease of insertion into a vein (not shown). The beveled end 22 and the plurality of transverse holes 20 allow blood to flow optimally through each and into the vein.

The graft-catheter 10 may be made of ePTFE with the catheter section 14 dip-coated with a polyurethane outer coating 18. Alternatively, the entire graft-catheter 10 may be dip-coated to form a polyurethane outer coating over the ePTFE material. The graft-catheter 10 may be formed as one piece from the ePTFE material or as two pieces with the graft section 12 and the catheter section 14 joined by methods such as molding or suturing. The polyurethane outer coating 18 provides stiffness for the catheter section 14 that will be inserted into a vein, as discussed in further detail below. For example, the polyurethane coating or material for the various embodiments may be comprised of polyether, polyester, or polycarbonate and be either aromatic or aliphatic and have a durometer value ranging from 70 A through 65 D. The polyurethane outer coating 18 provides a degree of stiffness to the catheter section 14 without adding significantly to the diameter of the catheter section 14 as the result would be if using materials such as silicone to achieve the same degree of stiffness.

Figure 2:
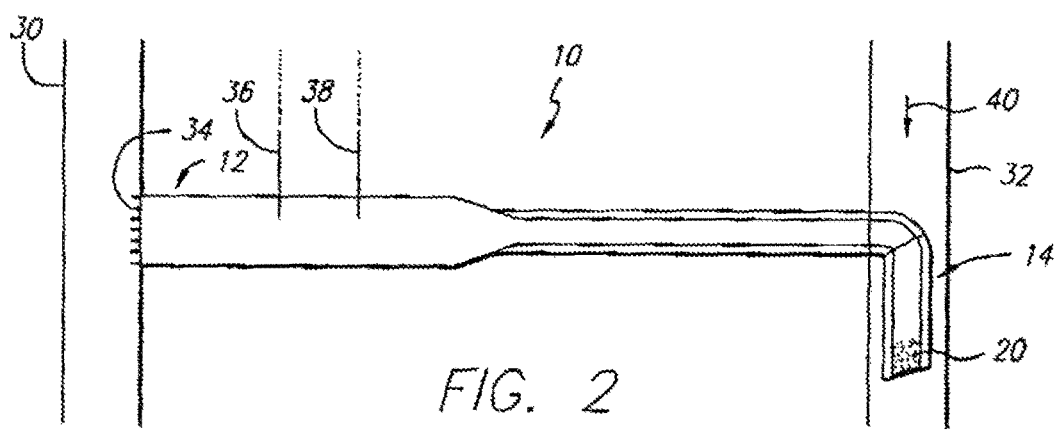
FIG. 2 is a side sectional view in accordance with a first embodiment of the present invention illustrating an interconnection between an artery and a vein.

FIG. 2 illustrates a side sectional view in accordance with a first embodiment of the present invention of an interconnection between the arterial and venous systems. The graft-catheter 10 provides a subcutaneous connection between an artery 30 and a vein 32. Alternatively, if desired, a portion of the graft-catheter 10 may exit through the skin (not shown) to provide access to the graft-catheter 10 without having to insert needles through the skin in order to reach the graft-catheter 10. The graft section 12 may be sutured to an opening in the artery 30 at a graft end 34 and the catheter section 14 may be inserted into the vein 32 by various methods, as known in the art, such as the cutdown method or via an introducer, and the vein may be self-sealing around the catheter section 14 or it may be sutured to the vein. The catheter section 14 is inserted into the vein 32 so that it lies within the vein 32 with the plurality of transverse holes 20 downstream (as shown by a blood flow direction indicator 40) from the point in the vein 32 where the catheter section 14 enters. This helps to prevent complications such as neointimal hyperplasia and thrombosis.

As an example, a first needle 36 and a second needle 38 may penetrate the skin (not shown) to gain access to the graft-catheter 10 by puncturing the graft section 12 or, alternatively, by entering a needle receiving port incorporated into the graft-catheter 10, as discussed in further detail below. The needles 36, 38 allow a complete blood circuit to and from the patient through the graft-catheter 10, with blood exiting through the first needle 36, into, for example, a hemodialysis machine (not shown), and then returning to the graft-catheter 10 at a downstream position through the second needle 38, where it will then flow into the vein 32. As noted above, the graft section 12 may be comprised of ePTFE which would require maturing prior to puncturing by the needles 36, 38 or, alternatively, the graft section 12 may be coated with polyurethane, which would then allow immediate insertion of the needles due to the self-sealing qualities of polyurethane.

Figure 3:
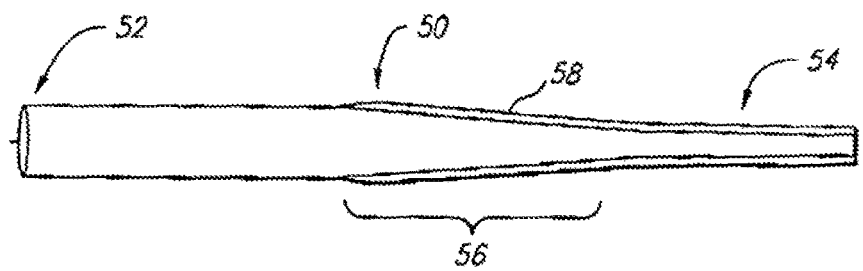
FIG. 3 is a side sectional view in accordance with a second embodiment of the present invention.

FIG. 3 shows a side sectional view of a graft-catheter 50 in accordance with a second embodiment of the present invention. The graft-catheter 50, similar to the graft-catheter 10, has a graft section 52 and a catheter section 54, but a tapered region 56 tapers in a much more gradual fashion than the tapered region 16 of the graft-catheter 10. The more gradual transition from the graft section 52 to the catheter section 54 provides superior blood flow and improvements in the blood flow mechanics as the blood transitions through the graft-catheter 50 from an artery to a vein. As discussed above, the graft-catheter 50 may be comprised of ePTFE with a polyurethane coating 58 over the catheter section 54 (as shown) or, alternatively, the polyurethane coating 58 may completely coat the graft-catheter 50. Furthermore, the graft-catheter 50 may include an inner polyurethane coating (not shown) as discussed in further detail for certain of the following embodiments.

Figure 4:
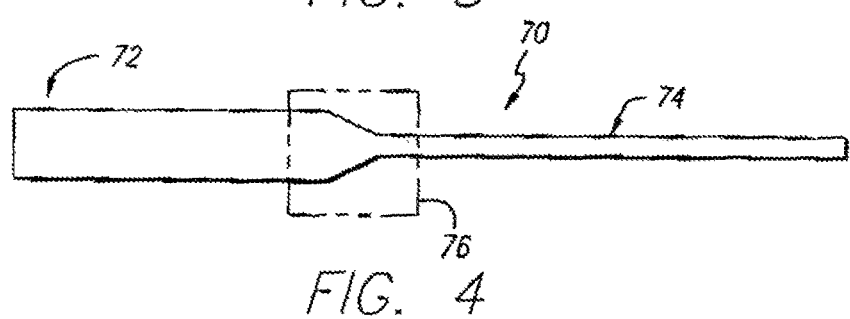
FIG. 4 is a side sectional view in accordance with a third embodiment of the present invention.

FIG. 4 illustrates a side sectional view of a graft-catheter 70 in accordance with a third embodiment of the present invention. The graft-catheter 70 has a graft section 72 and a catheter section 74. The graft section 72 may be comprised of ePTFE and the catheter section 74 may be comprised of polyurethane. The graft section 72 may be joined to the catheter section 74 in region 76 by an injection molded hub process, as known in the art. This eliminates having to coat the catheter section with polyurethane, as discussed above, but the graft section 72 may, if desired, be coated with polyurethane to provide stiffness and aid in sealing puncture sites. As an alternative to the injection molded hub process, the graft section 72 may be adhesive bonded or sutured to the catheter section 74 either prior to insertion in the patient or during a surgical procedure to insert the graft-catheter 70 or to replace one of its sections.

Figure 5:
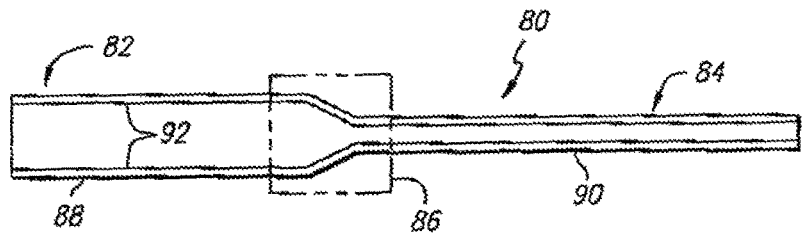
FIG. 5 is a side sectional view in accordance with a fourth embodiment of the present invention.

FIG. 5 illustrates a side sectional view of a graft-catheter 80 in accordance with a fourth embodiment of the present invention. The graft-catheter 80, similar to the graft-catheter 70, has a graft section 82 and a catheter section 84. The graft section 82 may be comprised of ePTFE and the catheter section 84 may be comprised of polyurethane with the graft section 82 and the catheter section 84 joined in region 86 by an injection molded hub process. The internal surface of the graft-catheter 80 is molded or coated with an inner polyurethane coating 92 that is applied to the ePTFE 88 of the graft section 82 and the polyurethane material 90 of the catheter section 84. The inner polyurethane coating 92 smoothes the inner surface of the graft-catheter 80, so that superior blood contact characteristics will be achieved, and provides the bloodstream with a surface that exhibits no change in surface chemistry throughout the length of the graft-catheter 80. The inner polyurethane coating 92 may be utilized in any of the embodiments, for example with the first embodiment discussed above.

In addition, the inner polyurethane coating 92 will help seal the graft section 82 after puncture by a needle so that the graft-catheter 80 allows needle access immediately after insertion into a patient. As discussed above, most grafts require a maturation period during which cell or protein deposition on the internal surfaces of the graft occurs along with tissue in-growth on the external surfaces. In combination, the protein deposition and cellular in-growth allows the graft material to quickly seal after needle puncture. The inner polyurethane coating 92 allows needle access to the graft section 82 immediately after insertion of the device into a patient because the inner polyurethane coating 92 seals the inner lumen access point instantly after removal of the needle. Because the outside of the graft section 82 is not coated, normal tissue in-growth can take place. This increases the stability of the graft-catheter 80 in the tissue and assists in anchoring the graft-catheter 80.

Figure 6:
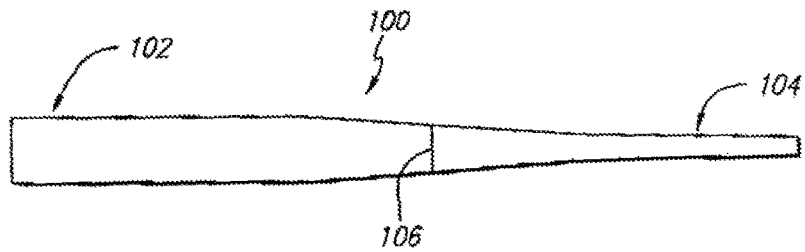
FIG. 6 is a side sectional view in accordance with a fifth embodiment of the present invention.

FIG. 6 illustrates a side sectional view of a graft-catheter 100 in accordance with a fifth embodiment of the present invention. The graft-catheter 100 has a graft section 102 and a catheter section 104. The graft-catheter 100 may be comprised of polyurethane with the graft section 102 and the catheter section 104 joined at a joint 106 by processes, as known in the art, such as simultaneous molding or adhesive bonding. Alternatively, the graft-catheter 100 may be formed from polyurethane as a single piece with no joints in the transition from the graft section 102 to the catheter section 104. The transition between the graft section 102 and the catheter section 104 may vary from a sharp taper, as shown in FIG. 1, to a long gradual taper, as shown in FIG. 3. By having the entire graft-catheter 100 made of polyurethane, superior flow dynamics may be achieved in comparison to other materials such as ePTFE or silicone rubber, and the joint 106 will be smooth and strong. By making the graft section 102 of polyurethane, there is no need to wait for healing or a maturing process to take place, as with ePTFE, prior to puncturing the graft section 102 with a needle. In addition, the exact characteristics of polyurethane, as discussed above, may vary between the graft section 102 and the catheter section 104 so that the optimal characteristics for each section can be provided.

Polyurethane has the additional advantage of being modifiable by various methods that enhance its surface characteristics. These methods may include a surface modifying end group (SME), surface modifying macromolecule (SMR), treatment with anti-coagulant agents such as heparin, and other polyurethane modification techniques such as ion beam implantation, gas plasma treatment, or coating with a hydrogel such as polyvinylpyrrolidone (PVP), polyethyleneglycol (PEG), and/or a polyethyleneoxide (PEO), as is known in the art. These methods will improve compatibility and blood flow and help to prevent thrombosis and hyperplasia.

Figure 7:
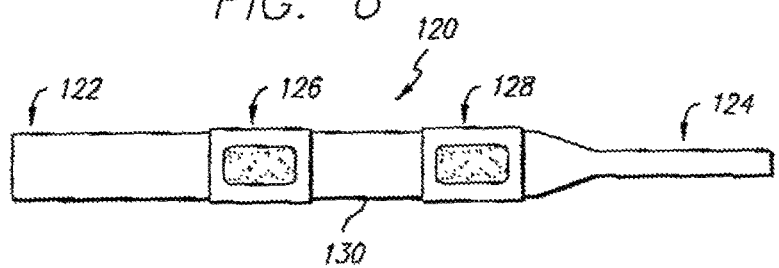
FIG. 7 is a side sectional view in accordance with a sixth embodiment of the present invention.

FIG. 7 illustrates a side sectional view of a graft-catheter 120 in accordance with a sixth embodiment of the present invention. The graft-catheter 120 has a graft section 122 and a catheter section 124. Between the graft section 122 and the catheter section 124, there are two needle-receiving ports 126, 128 for insertion of needles. The needle receiving ports 126, 128 are coupled by a coupling section 130. Alternatively, there may be only one needle receiving site with two separate needle access points or ports. The graft-catheter 120 may incorporate features from the various embodiments discussed above. For example, the materials utilized may comprise ePTFE, polyurethane, or some combination thereof, that may include a polyurethane coating, for the graft section 122, the coupling section 130, and the catheter section 124. With the presence of the needle receiving ports 126, 128, the graft-catheter 120 may be used without delay for healing, even if the graft section 122 is made of ePTFE, because the needles will penetrate the self-sealing needle receiving ports 126, 128 rather than the ePTFE material.

Figure 8:
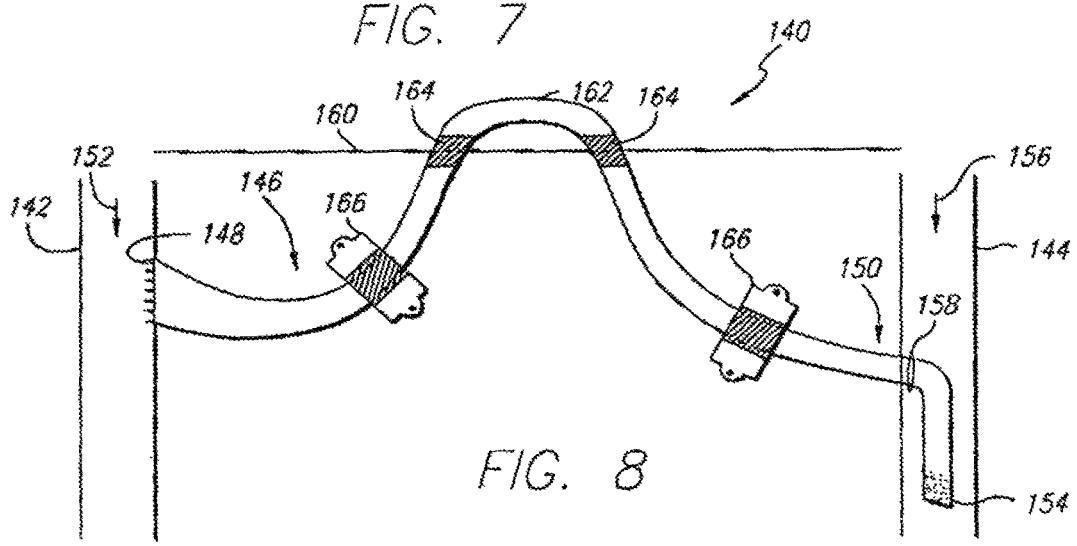
FIG. 8 is a side sectional view in accordance with a seventh embodiment of the present invention illustrating an interconnection between an artery and a vein.

FIG. 8 illustrates a side sectional view of a graft-catheter 140, in accordance with a seventh embodiment of the present invention, showing an interconnection between the arterial and venous systems. The graft-catheter 140 provides a subcutaneous connection between an artery 142 and a vein 144, but could provide an interconnection between any two vascular points. The graft-catheter 140 may utilize various aspects of the embodiments discussed above, such as needle receiving ports, various materials, coatings, or processes. A graft section 146 may be sutured to an opening in the artery 142 at a graft end 148 and a catheter section 150 may be inserted into the vein 144 by various methods such as by the cutdown method or Seldinger technique. The graft section 146 may be angled to the artery 142, towards the direction of blood flow as indicated by a blood flow direction indicator 152, so as to improve blood flow within the graft-catheter 140. The catheter section 150 is inserted into the vein 144 so that it lies within the vein 144 with a catheter section end 154 having a plurality of transverse holes located downstream (as shown by a blood flow direction indicator 156) from the opening in the vein 144 through which the catheter section 150 entered the vein 144.

Additionally, as noted above, a portion 162 of the graft-catheter 140 may reside external to a skin surface 160 to provide access to the graft-catheter 140 without having to penetrate the skin or body with needles. The portion 162 may comprise a portion of the graft section 146 or the catheter section 150 and may further comprise a port for needle access, as discussed above, or a hub attachment site or other types of connectors for ease of use and access.

The portion of the catheter section 150 within the vein 144 may be secured by various securement devices, as known in the art, such as a venous cuff 158. The venous cuff 158 also aids in sealing the vein around the catheter section 150, with the option of also suturing the catheter section 150 to the vein 144. In addition, the portion 162 may be secured at the body surface 160 with a cuff 164. The cuff 164 may be comprised of a material such as polyester. The graft-catheter 140 may be further secured with a movable internal suture wing 166 that is sutured to the internal subcutaneous tissues (not shown). This minimizes movement and resists the tendency of the graft-catheter 140 to slide out of the artery 142 (if attached without an anastomosis) or the vein 144. The internal suture wing may be comprised of polyurethane or silicone rubber.

Figure 9A:
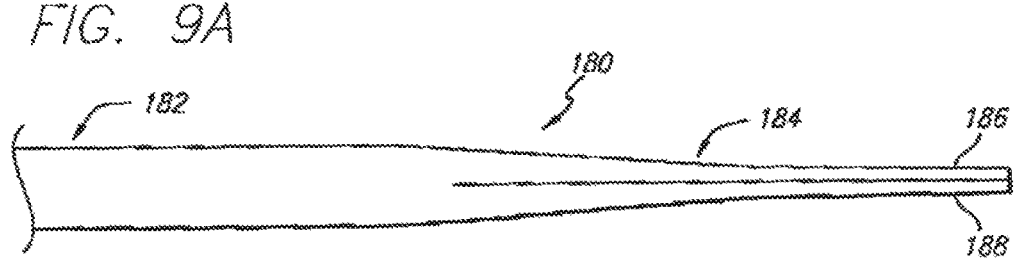
FIG. 9(a) is a side sectional view in accordance with an eighth embodiment of the present invention illustrating a dual lumen configuration.
Figure 9B:
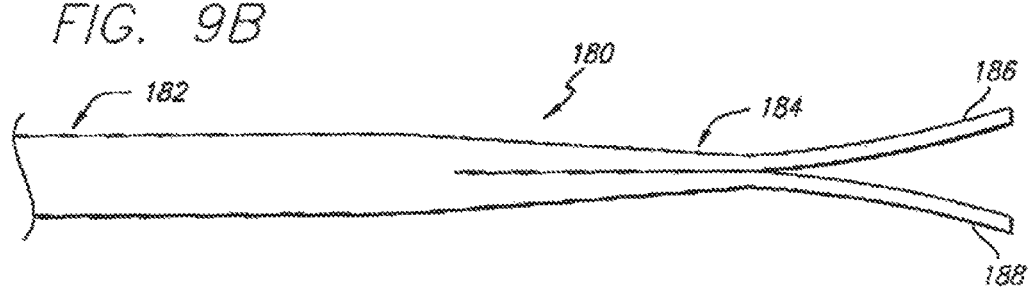
FIG. 9(b) illustrates the dual lumen configuration of FIG. 9(a) with the lumens separated.

FIG. 9(a) is a side sectional view of a graft-catheter 180, in accordance with an eighth embodiment of the present invention, illustrating a dual lumen configuration. The graft-catheter 180 has a graft portion 182 and a catheter portion 184, with the catheter portion 184 comprised of a dual lumen configuration having a first lumen 186 and a second lumen 188. This allows the catheter portion 184 to be placed in two veins simultaneously, which reduces arterial flow to each vein as well as arterial pressurization in the vein. This results in less trauma to the vein's intima and wall. As shown in FIG. 9(b), the catheter portion 184 could also be split so that the first lumen 186 and the second lumen 188 are separated as shown. This simulates the Ash Split Catheter, as known in the art, which may provide an increase in patency to the graft-catheter 180.

Figure 10:
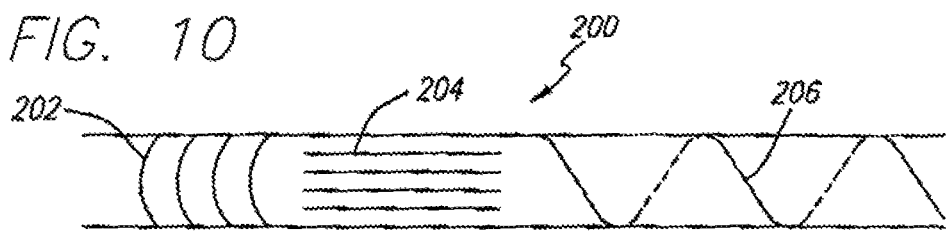
FIG. 10 is a side sectional view in accordance with a ninth embodiment of the present invention illustrating support devices.

FIG. 10 is a side sectional view of a portion of a graft-catheter 200, in accordance with a ninth embodiment of the present invention, illustrating various types of support devices. These support devices may be added to any portion of the graft-catheter 200 to provide rigidity or structural integrity while preventing excessive bending, kinking, crushing, or twisting. The support devices may comprise a circular support 202, a longitudinal spline 204, a spiral wrap 206, or some combination of the support devices. Alternatively, additional layers or coatings of polyurethane may be added at stress points.

Figure 11A:
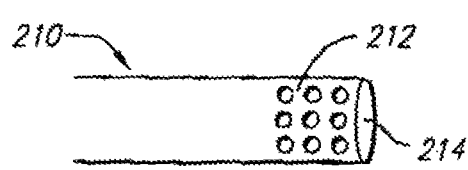
FIG. 11(a) is a side sectional view in accordance with a tenth embodiment of the present invention illustrating a first hole pattern.

FIG. 11(a) shows a side sectional view, of a catheter portion 210, in accordance with a tenth embodiment of the present invention. The catheter portion 210 illustrates a first hole pattern 212 near an end 214 of the catheter portion 210. As discussed above, a plurality of transverse holes may be provided near the end of the catheter for optimal blood flow and dispersion, with a portion of the blood flowing through the transverse holes. The first hole pattern 212, for catheter portion 210, has a circular hole pattern. The number of holes may vary as well as the specific column or row alignment and whether the pattern continues around the entire circumference of the catheter portion 210 or only some portion of the entire circumference.

Figure 11B:
FIG. 11(b) is a side sectional view in accordance with an eleventh embodiment of the present invention illustrating a second hole pattern.

FIG. 11(b) shows a side sectional view, of a catheter portion 220, in accordance with an eleventh embodiment of the present invention. The catheter portion 220 illustrates a second hole pattern 222 near an end 224 of the catheter portion 220. The second hole pattern 222 is a spiral pattern. As above for FIG. 11a, the number of holes may vary as well as the specific pattern and configuration. FIG. 11a and FIG. 11b are examples of the types of hole patterns, but it should be understood that many other patterns may be utilized and the present invention is not limited by these examples. For example, the hole pattern may comprise a random pattern, staggered, offset, or some variation of the above. In addition, holes may be round, oval, square, triangular, or some other geometric shape.

The lumen shape of the graft-catheter for the various embodiments may also vary. For example, the lumen configuration may be oval, round, hexagonal, or square. Furthermore, the end of the catheter portion or tip may be blunt, staggered, or beveled, as discussed above, to aid in its insertion into a vein.

Figure 12A:
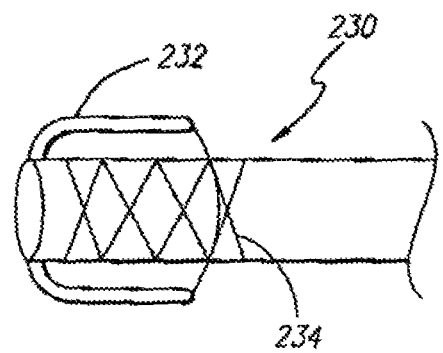
FIG. 12(a) is a side sectional view in accordance with a twelfth embodiment of the present invention illustrating a graft securement device.
Figure 12B:
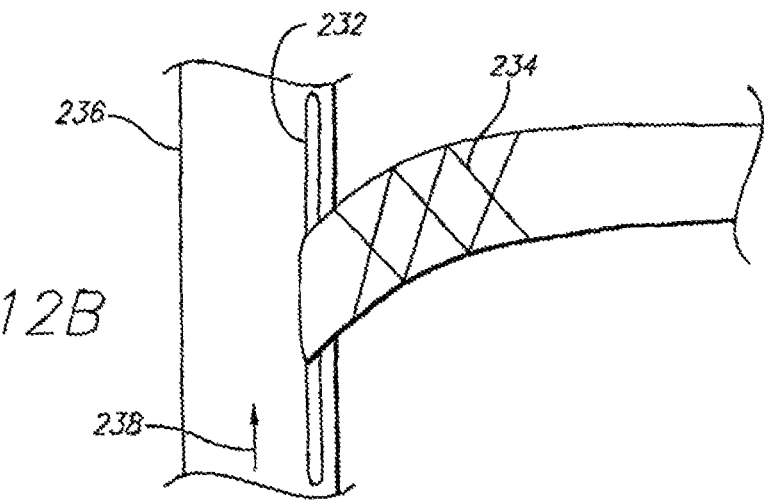
FIG. 12(b) illustrates the graft securement device of FIG. 12(a) inserted into an artery.

FIG. 12(a) shows a side sectional view of a graft portion 230, in accordance with a twelfth embodiment of the present invention. The graft portion 230 may be inserted into an artery via a sheath method; thus no cut down or anastomosis is necessary. The graft portion 230 has a retaining ring 232, but could be replaced by or include a cuff, as discussed above, that when inserted into an artery 236, as illustrated in FIG. 12(b), will secure the graft portion 230 within the artery 236. The graft portion 230 may also comprise an internalized or externalized stent 234 to provide strength so as to prevent the graft portion 230 from being crushed by the artery 236. Therefore, the procedure may take place via an introducer and split sheath method, as known in the art. As shown in FIG. 12(a), the retaining ring 232 would be folded down when placed through a sheath, prior to insertion into the artery 236. As shown in FIG. 12(b), after insertion into the artery 236, the retaining ring 232 would extend to secure the graft portion 230 in the artery 236. The graft portion 230 may also be angled as shown towards the direction of blood flow as indicated by a blood flow direction indicator 238.

Figure 13:
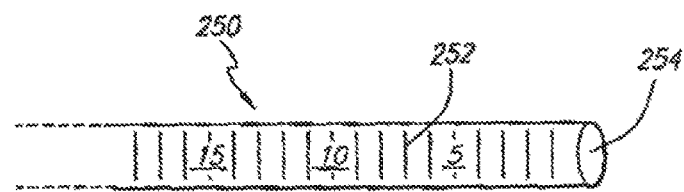
FIG. 13 is a side sectional view in accordance with a thirteenth embodiment of the present invention illustrating catheter depth markings.

FIG. 13 shows a side sectional view of a catheter portion 250, in accordance with a thirteenth embodiment of the present invention. The catheter portion 250 illustrates a series of depth markings 252 beginning at a catheter portion end 254. The depth markings 252 make it possible for a physician to insert the catheter portion 250 into a vein (not shown), while being able to easily monitor the depth of penetration into the vein. The catheter portion 250 could also include a radiopaque strip to provide improved x-ray visualization. Alternatively, for the various embodiments discussed, the entire graft-catheter or some portion may include a radiopaque strip or coated with a radiopaque polyurethane outer or inner coating. The graft or catheter portion could also include an echogenic coating, thereby allowing a physician to visualize and access the preferred portion of the graft-catheter using ultrasound.

Having thus described a preferred embodiment of the graft-catheter, it should be apparent to those skilled in the art that certain advantages of the within system have been achieved. It should also be appreciated that various modifications, adaptations, and alternative embodiments thereof may be made within the scope and spirit of the present invention. For example, a graft-catheter has been illustrated to show an embodiment of the present invention, but it should be apparent that the inventive concepts described above would be equally applicable to a graft or catheter, as known in the art. The invention is further defined by the following claims.

What is claimed is:

1. A method of medical treatment, comprising:
providing a vascular access device having a length from a distal end to a proximal end and comprising:
a unitary tubular wall having a first end defining a graft portion and a second end defining a catheter portion,
the graft portion including a wall defining a single lumen having a substantially constant diameter,
the catheter portion including a wall defining a lumen in fluid communication with the single lumen of the graft portion, a distal end of the catheter portion having a diameter smaller than the substantially constant diameter of the graft portion and including a plurality of transverse holes, wherein the vascular access device has a smooth inner surface that exhibits no change in surface chemistry throughout the length of the vascular access device;
suturing a proximal end of the graft portion to a side opening of an artery; and
placing the catheter portion into a vein without an anastomosis by inserting the distal end of the catheter portion into a side opening of a vein such that the distal end lies within the vein at a location downstream from the side opening of the vein,
wherein the providing a vascular access device step includes providing a vascular access device wherein the graft portion wall consists of polyurethane having a first durometer value, and wherein the catheter portion wall consists of polyurethane having a second durometer value different from the first durometer value.

2. A method of medical treatment, comprising:
providing a vascular access device having a length from a distal end to a proximal end and comprising:
a unitary tubular wall having a first end defining a graft portion and a second end defining a catheter portion,
the graft portion including a wall defining a single lumen having a substantially constant diameter,
the catheter portion including a wall defining a lumen in fluid communication with the single lumen of the graft portion, a distal end of the catheter portion having a diameter smaller than the substantially constant diameter of the graft portion and including a plurality of transverse holes, wherein the vascular access device has a smooth inner surface that exhibits no change in surface chemistry throughout the length of the vascular access device;
suturing a proximal end of the graft portion to a side opening of an artery; and
placing the catheter portion into a vein without an anastomosis by inserting the distal end of the catheter portion into a side opening of a vein such that the distal end lies within the vein at a location downstream from the side opening of the vein,
wherein the providing a vascular access device step includes providing a vascular access device having a gradual taper between the substantially constant diameter of the graft portion and the distal end of the catheter portion, wherein the gradual taper extends for a length longer than half an end to end length of the graft portion.

* * * * *